United States Patent [19]

Zak

[11] Patent Number: 5,475,147
[45] Date of Patent: Dec. 12, 1995

[54] PRODUCTION OF TERTIARY BUTYL HYDROPEROXIDE

[75] Inventor: Thomas S. Zak, West Chester, Pa.

[73] Assignee: ARCO Chemical Technology, L.P., Greenville, Del.

[21] Appl. No.: 325,751

[22] Filed: Oct. 19, 1994

[51] Int. Cl.⁶ .................... C07C 409/02; C07C 409/04
[52] U.S. Cl. .................... 568/569; 568/568; 568/570; 568/571; 568/910
[58] Field of Search .................... 568/568, 569

[56] References Cited

U.S. PATENT DOCUMENTS

| 2,845,461 | 7/1958 | Winkler et al. | 568/568 |
| 3,351,635 | 11/1967 | Kollar | 568/569 |
| 3,478,108 | 11/1969 | Grane | 568/569 |
| 4,408,081 | 10/1983 | Foster | 568/570 |
| 4,584,413 | 4/1986 | Thornton et al. | 568/569 |
| 5,149,885 | 9/1992 | Jubin, Jr. | 568/569 |
| 5,196,597 | 3/1993 | Cochran et al. | 568/571 |
| 5,243,084 | 9/1993 | Cochran et al. | 568/571 |
| 5,399,777 | 3/1995 | Mueller | 568/569 |

Primary Examiner—Warren B. Lone
Attorney, Agent, or Firm—William C. Long

[57] ABSTRACT

Isobutane containing a significant amount of isobutylene is treated at conditions effective to oligomerize a predominance of the isobutylene, isobutane substantially free of isobutylene is separated from the oligomer products, and the isobutane substantially free of isobutylene is oxidized to tertiary butyl hydroperoxide.

3 Claims, No Drawings

PRODUCTION OF TERTIARY BUTYL HYDROPEROXIDE

BACKGROUND OF THE INVENTION

1. Field of the Invention

The present invention relates to the production of tertiary butyl hydroperoxide from isobutane which contains a small amount of isobutylene and especially to a process which involves oligomerizing the isobutylene, separating the oligomer product, and oxidizing the isobutane substantially free of isobutylene to form tertiary butyl hydroperoxide.

2. Description of the Prior Art

Methods are known for the production of tertiary butyl hydroperoxide by the molecular oxygen oxidation of isobutane at elevated temperature and pressure. In this regard, attention is drawn to U.S. Pat. No. 2,845,461 of Winkler, et al., to U.S. Pat. No. 3,478,108 of Grane and to U.S. Pat. No. 4,408,081 of Foster, et al. Frequently, the tertiary butyl hydroperoxide product from the oxidation is used to epoxidize olefins such as propylene by procedures such as those described in basic U.S. Pat. No. 3,351,635.

A problem which has existed in this technology is that the isobutane which is fed to the oxidation may contain a significant concentration of butenes, notably isobutylene. The presence of isobutylene in the oxidation feed has an adverse effect on the selective production of tertiary butyl hydroperoxide in the oxidation process. Illustratively, the presence of as little as 1% isobutylene in the isobutane feed to the oxidation results in a decrease of the order of 8% by weight in tertiary butyl hydroperoxide production and a substantial increase in the formation of undesirable by products.

BRIEF DESCRIPTION OF THE INVENTION

In accordance with the present invention, a process is provided whereby an isobutane stream which contains substantial amounts of isobutylene is first treated at conditions effective to oligomerize the contained isobutylene to dimer, trimer and/or higher derivatives; the isobutane is then separated from the oligomerization products by distillation, and the thusly obtained isobutane substantially free of isobutylene is oxidized with molecular oxygen to tertiary butyl hydroperoxide.

DETAILED DESCRIPTION

Isobutane feed streams which are treated in accordance with the invention are those which contain small but significant amounts of isobutylene, i.e. 0.1 to about 5 wt % isobutylene. The impure isobutane stream is treated at conditions which effectively oligomerize the contained isobutylene to oligomeric products such as the dimer, trimer and the like. The oligomerization conditions are such that a predominance of the isobutylene is converted, preferably 60–100%. In especially preferred practice, the oligomerization conditions involve passing isobutane containing isobutylene impurity in the liquid phase through a bed of strong acid ion exchange resin at elevated temperature. Illustrative contact temperatures are 100°–250° F., preferably 130°–200° F. at WHSV of 1–100, preferably 10–30. Pressure is sufficient to maintain the liquid phase, e.g. 100 to 500 psig. Other known oligomerization procedures can also be employed.

Oligomeric product is separated from the treated isobutane stream and the isobutane substantially free of contained isobutylene is oxidized in the liquid phase to tertiary butyl hydroperoxide in accordance with known procedures.

The isobutane oxidation reaction conditions are those which are normally used for this reaction as described, for example, in Winkler, et al. U.S. Pat. No. 2,845,461. Generally, reaction temperatures in the range of 100° C. to 200° C., preferably 120° C. to 150° C. are employed. Pressures in the range of 200 to 500 psig, preferably 300 to 450 psig are employed. Residence times in the oxidation zone of 3 to 15 hours, preferably 5 to 10 hours are suitable. It is preferred to use oxygen as the oxidant, although the use of oxygen in admixture with minor amounts of an inert gas such as nitrogen can be used.

The following example illustrates the invention.

An isobutane stream containing isobutylene was passed in the liquid phase over a strong sulfonic acid ion exchange resin, Amberlyst 15, at 180° F., 400 psig and 20 WHSV. The oligomeric product was separated as a heavies from the isobutane by distillation with better than 95% effectiveness. The following table shows the isobutane stream composition before and after the oligomerization treatment.

TABLE

| Component, Wt % | Feed | Product |
| --- | --- | --- |
| isobutylene | 0.26 | 0.008 |
| butene-1 | 0.25 | 0.04 |
| cisbutene-2 | — | 0.05 |
| transbutene-2 | — | 0.11 |
| diisobutylene | — | 0.16 |
| triisobutylene | — | 0.14 |
| n butane | 0.015 | 0.015 |
| isobutane | balance | balance |

From the above it can be seen that about 97% of the isobutylene was oligomerized as well as about 20% of the normal butene. The oligomerization product was 53% diisobutylene and 47% triisobutylene.

Purified isobutane was separated from oligomer product by distillation and the purified isobutane was oxidized with molecular oxygen in the liquid phase at 135° C. and 400 psig to produce a product mixture comprised of 59.0 wt % tertiary butyl hydroperoxide, 35.5 wt % tertiary butyl alcohol and 5.5 wt % others.

By contrast when the isobutylene-containing isobutane is oxidized at the same conditions without prior isobutylene removal, there is obtained a product mixture comprised of 56.1 wt % tertiary butyl hydroperoxide, 37.5 wt % tertiary butyl alcohol and 6.4 wt % others.

I claim:

1. A process for the production of tertiary butyl hydroperoxide which comprises treating an isobutane feedstream containing a significant amount of isobutylene impurity at conditions effective to oligomerize a predominance of the said isobutylene, distilling isobutane reduced in isobutylene content from the products of oligomerization, and oxidizing the distilled isobutane reduced in isobutylene content with molecular oxygen to form tertiary butyl hydroperoxide.

2. The process of claim 1 wherein the isobutane feedstream contains 0.1–5 wt % isobutylene, 3. The process of claim 1 wherein a strong acid ion exchange resin is used to oligomerize the isobutylene.

* * * * *